(12) United States Patent
Loesel et al.

(10) Patent No.: US 7,717,905 B2
(45) Date of Patent: May 18, 2010

(54) TIME-RESOLVED SCANNING PATTERNS FOR INTRASTROMAL SURGERY

(75) Inventors: Frieder Loesel, Mannheim (DE); Tobias Kuhn, Jena (DE)

(73) Assignee: Technolas Perfect Vision GmbH, Heidelberg (DE)

( * ) Notice: Subject to any disclaimer, the term of this patent is extended or adjusted under 35 U.S.C. 154(b) by 1474 days.

(21) Appl. No.: 10/978,613

(22) Filed: Nov. 1, 2004

(65) Prior Publication Data

US 2006/0095023 A1    May 4, 2006

(51) Int. Cl.
*A61F 9/008* (2006.01)
(52) U.S. Cl. ............. 606/4; 606/2; 606/3; 606/6; 128/898
(58) Field of Classification Search ............... 606/1–6; 607/88, 89; 128/898
See application file for complete search history.

(56) References Cited

U.S. PATENT DOCUMENTS

| | | | |
|---|---|---|---|
| 3,769,963 | A | 11/1973 | Goldman et al. |
| 4,391,275 | A * | 7/1983 | Fankhauser et al. ............ 606/4 |
| 4,665,913 | A | 5/1987 | L'Esperance, Jr. |
| 4,669,466 | A | 6/1987 | L'Esperance |
| 4,732,148 | A | 3/1988 | L'Esperance, Jr. |
| 4,770,172 | A | 9/1988 | L'Esperance, Jr. |
| 4,773,414 | A | 9/1988 | L'Esperance, Jr. |
| 4,941,093 | A | 7/1990 | Marshall et al. |
| 4,988,348 | A | 1/1991 | Bille |
| 5,549,632 | A | 8/1996 | Lai |
| 5,984,916 | A | 11/1999 | Lai |
| 5,993,438 | A * | 11/1999 | Juhasz et al. ................... 606/5 |
| 6,010,497 | A * | 1/2000 | Tang et al. ..................... 606/5 |
| 6,231,566 | B1 | 5/2001 | Lai |
| 6,322,556 | B1 * | 11/2001 | Gwon et al. .................... 606/6 |
| 6,325,792 | B1 | 12/2001 | Swinger et al. |
| 6,610,050 | B2 * | 8/2003 | Bille ............................ 606/5 |
| 6,610,051 | B2 | 8/2003 | Bille |
| 6,805,694 | B2 * | 10/2004 | Donitzky ....................... 606/5 |

(Continued)

FOREIGN PATENT DOCUMENTS

DE    103 34 109 A1    2/2005

OTHER PUBLICATIONS

Heisterkamp A. et al., "*Optimizing Laser Parameters for Intrastromal Incision With Ultra-Short Laser Pulses*", Jul. 2001, vol. 98, No. 7, pp. 623-628.

*Primary Examiner*—Henry M Johnson, III
*Assistant Examiner*—Jeffrey B Lipitz
(74) *Attorney, Agent, or Firm*—Nydegger & Associates

(57) ABSTRACT

A system and method for performing laser induced optical breakdown (LIOB) in corneal tissue of an eye requires calculating a pattern of focal spots. LIOB is then induced at a first focal spot, and is continued at a plurality of interim focal spots within a time period $\tau$. Each focal spot has a diameter "$d_1$" and generates a temporal cavitation bubble of diameter "$d_2$". It then collapses within time "$\tau$" to a substantially stationary diameter "$d_3$", with ($d_1 \leq d_3 \leq d_2$). Importantly, each focal spot is located more than "$d_2$" from every other interim focal spot within the time period of "$\tau$". At the time "$\tau$", a second focal spot in the pattern can be generated at a distance "$d_3$" from the first focal spot. This process is then continued with another plurality of interim focal spots being generated within another time period "$\tau$".

15 Claims, 3 Drawing Sheets

U.S. PATENT DOCUMENTS

| | | | |
|---|---|---|---|
| 7,131,968 B2 * | 11/2006 | Bendett et al. | 606/10 |
| 2003/0229339 A1 * | 12/2003 | Bille | 606/5 |
| 2004/0039378 A1 * | 2/2004 | Lin | 606/6 |
| 2004/0243111 A1 * | 12/2004 | Bendett et al. | 606/5 |
| 2004/0243112 A1 | 12/2004 | Bendett et al. | |
| 2005/0165386 A1 * | 7/2005 | Kurtz et al. | 606/4 |
| 2006/0106371 A1 * | 5/2006 | Muhlhoff et al. | 606/5 |
| 2008/0208104 A1 * | 8/2008 | Bragagna et al. | 604/20 |

\* cited by examiner

TIME-RESOLVED SCANNING PATTERNS FOR INTRASTROMAL SURGERY

FIELD OF THE INVENTION

The present invention pertains generally to systems and methods for creating spot patterns for ophthalmic refractive laser surgery. More particularly, the present invention pertains to systems and methods which minimize the residual effects from laser induced optical breakdown (LIOB) at earlier laser focal points, on LIOB at subsequent laser focal points. The present invention is particularly, but not exclusively, useful for systems and methods wherein LIOB at adjacent focal points in the stroma (transparent material) is performed in accordance with a predetermined spatial and temporal separation.

BACKGROUND OF THE INVENTION

During an ophthalmic laser surgical procedure, wherein stromal tissue within the cornea is ablated, the ablation is caused by an effect known as Laser Induced Optical Breakdown (LIOB). Typically, LIOB in the stroma is accomplished using pulsed laser beams that may have pulse repetition rates as high as 10 KHz. In detail, the LIOB effect of successive individual laser pulses is cumulative. Each individual laser pulse, however, can be considered separately.

For an individual laser pulse, it happens during LIOB that the tissue being ablated may be subjected to several different phenomena. For one, tissue that is peripheral to the ablated tissue is subject to adverse side effects, such as tearing (mechanical damage) and scorching (thermal damage). It is known, however, that these particular adverse side effects can be avoided if the pulse energy density is minimized. On the other hand, the pulse energy density must be above the tissue threshold in order for LIOB to occur. With these countervailing considerations in mind, it has been determined that a laser pulse having the following characteristics can cause LIOB in stromal tissue, while avoiding adverse mechanical or thermal side effects on peripheral tissue.

Laser Pulse
Pulse Length (duration): 1-1000 femtoseconds
Energy Density: 1-10 J/cm$^2$
Focal Spot Size: 1-10 μm diameter
Pulse Repetition Rate: multi KHz Despite the adverse, but avoidable, side effects on peripheral tissue noted above, LIOB will still affect stromal tissue in at least three other different, identifiable ways. These are: 1) plasma formation; 2) shock wave generation; and 3) cavitation bubbles. Schematically, these three phenomena are shown in FIG. 1 of the drawings.

Referring for the moment to FIG. 1 in the drawings, the consequences of LIOB caused by a single laser pulse are illustrated in a spatial context. It is to be appreciated, however, these consequences also have a temporal context. First, a micro plasma is formed from tissue located within the focal spot of the laser pulse. Specifically, this plasma results from the evaporation of corneal tissue 10 in a tissue volume 12 that has a diameter "$d_1$" in the range of around 1-10 microns ($d_1$=1-10 μm). The formation of this plasma is then followed by a shock wave that radiates through the tissue 10. Typically, the shock wave extends from the center of volume 12 through a radius "r" that is approximately twenty microns (r≈20 μm). The shock wave, however, decays within a few nanoseconds. Nevertheless, despite its relatively short duration, the shockwave effect should be kept as small as possible by using pulse energies that are not too far above the threshold for LIOB.

Perhaps, the most pronounced adverse effect from LIOB at relatively low pulse energies is the creation of a cavitation bubble 14. Stated differently, at relatively low pulse energies there is typically no mechanical or thermal damage to peripheral tissue. Instead, a laser pulse having the parameters set forth above will induce LIOB that immediately results in a cavitation bubble 14 (see FIG. 1). There it will be seen that the bubble 14 has a diameter "$d_2$" that will generally be greater than about twice the diameter "$d_1$" of the tissue volume 12 ($d_2 \gtrsim 2d_1$). Although the cavitation bubble 14 will eventually decay, as generally indicated in FIG. 2, it has a time dependence that should be accounted for (N.B. FIG. 2 is only exemplary). In particular, FIG. 2 indicates the temporal influence of a cavitation bubble 14 may be considered as continuing through two decay periods. Specifically, the decay of the bubble 14 experiences a first relaxation rate of approximately 10 microns per second (10 μm/sec) during a first decay period, of time "τ". During "τ" the bubble 14 decays to a diameter "$d_3$" which is less than "$d_2$" but greater than "$d_1$" ($d_1 < d_2 > d_3$, with $d_3 > d_1$). Typically, the period "τ" is in the range of about 1-1000 μs and depends on a number of factors including pulse energy density. Thereafter, during a second decay period, the bubble 14 fully dissipates from the diameter "$d_3$" in about 15 to 30 minutes at a second relaxation rate of approximately half a micron per minute (0.5 μm/min).

In light of the above, it is an object of the present invention to provide a system and method for performing laser induced optical breakdown (LIOB) in a substantially transparent material (i.e. the cornea of an eye) wherein a predetermined time period "τ" is interposed between adjacent laser focal spots in a spot pattern. Another object of the present invention is to provide a system and method for performing laser induced optical breakdown (LIOB) in a substantially transparent material (i.e. the cornea of an eye) wherein a pattern of successive focal spots are both spatially and temporally separated from each other. Yet another object of the present invention is to provide a system and method for performing laser induced optical breakdown (LIOB) in a substantially transparent material (i.e. the cornea of an eye) wherein LIOB is induced at a location where the residual influence of earlier LIOB is effectively avoided. Still another object of the present invention is to provide a system and method for performing laser induced optical breakdown (LIOB) in a substantially transparent material (i.e. the cornea of an eye) which is easy to use, relatively simple to manufacture, and comparatively cost effective.

SUMMARY OF THE INVENTION

In accordance with the present invention, a method and a system are presented for performing laser induced optical breakdown (LIOB) in a substantially transparent material, such as the cornea of an eye. Specifically, the method includes a first step of calculating a pattern for a succession of laser focal spots in the material. Using this pattern, a surgical procedure is then performed wherein LIOB occurs at each focal spot in the pattern, in a volume of material having a diameter "$d_1$". Inherently, the LIOB at each focal spot results in the generation of a cavitation bubble that expands to a maximum diameter "$d_2$". In this process, however, the diameter of the temporal cavitation bubble "$d_2$" will increase to at least twice the diameter of the focal spot "$d_1$". It then collapses back toward the volume of the focal spot within a decay time "τ" to a substantially stationary diameter "$d_3$", with ($d_1 \leq d_3 \leq d_2$).

With the above in mind, once a pattern for LIOB has been determined, the actual procedure begins by inducing LIOB at a first focal spot. The procedure then continues by inducing LIOB at a plurality of interim focal spots within a time period "$\tau$". Importantly, each of the interim spots is located at a distance greater than "$d_2$" from every other interim focal spot that is generated within the time period of "$\tau$". At the end of the time period "$\tau$", a second focal spot in the pattern can then be generated at a distance "$d_3$" from the first focal spot. This process is then continued, with the second focal spot becoming a first focal spot. Another plurality of interim focal spots can then be generated within another time period "$\tau$". Importantly, as each focal spot is generated in the pattern, it must be separated by at least the distance "$d_2$" from every other focal spot that was generated within the immediately preceding time period "$\tau$".

As contemplated for the present invention, the distance "$d_1$" will be in a range of about 1 to 10 microns, and the distance "$d_2$" will be approximately equal to $2d_1$ ($d_2 \cong 2d_1$). Further, the time period "$\tau$" will be typically less than approximately two microseconds ($\tau \cong 2$ μs). Also, as contemplated for the present invention, LIOB will be induced by a laser pulse which has a duration in a range of 1-1000 fs, an energy density in the range of 1-10 J/cm$^2$, and a focal spot diameter of about 1-10 microns.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 3:
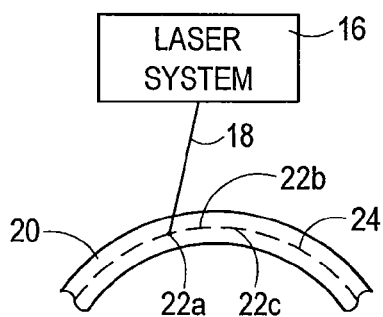
FIG. 3 is a schematic view of an operational laser beam as used for the present invention.

Referring to FIG. 3, an environment for the present invention is shown wherein a laser system 16 is used to focus a laser beam 18 into a transparent material 20, such as the stroma of an eye. As indicated, the laser beam 18 is focused to a succession of focal spots 22 in the transparent material 20, of which the focal spots 22a-c are only exemplary. Further, as also indicated in FIG. 3, the succession of focal spots 22 are maneuvered to create a pattern 24 within the material 20. For purposes of the present invention, the pattern 24 may be of any form or design well known in the pertinent art, such as a line, a curve, or a spiral.

Figure 1:
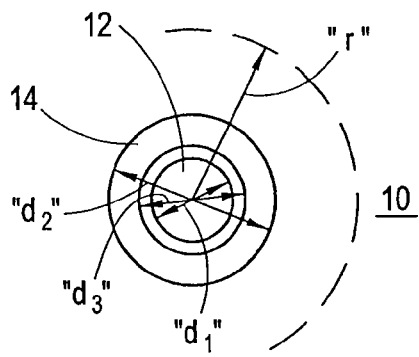
FIG. 1 is a representation of the spatial relationships between the ablated tissue, shock wave, and cavitation bubble that result from LIOB.
Figure 2:
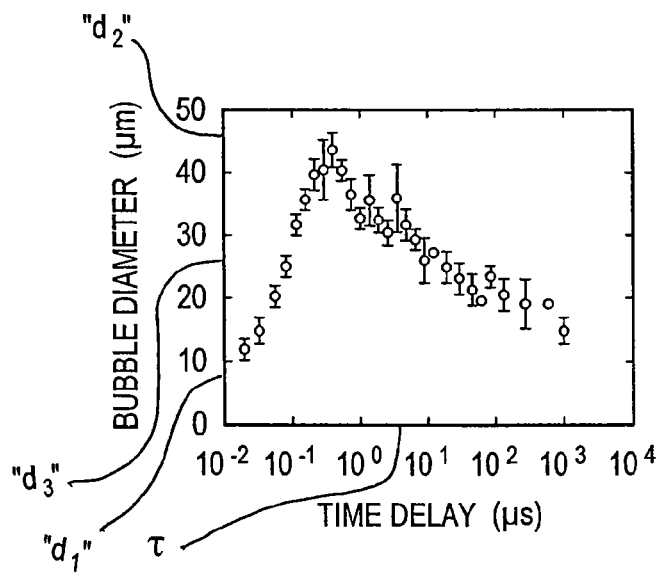
FIG. 2 is a graph showing the temporal decay of a typical cavitation bubble.

Preferably, the focal spots 22 in pattern 24 are created by a laser beam 18 which includes a train of laser pulses that have a pulse repetition rate in the multi KHz region (i.e. around 10 KHz or more). Further, each pulse in the train preferably has the following characteristics: 1) a pulse length (duration) in a range of 1-1000 femtoseconds; an energy density of 1-10 J/cm$^2$; and a focal spot size in a range of 1-10 μm diameter. As stated above, a laser pulse having these parameters will induce LIOB in a tissue volume 12 of the material 20 that has a diameter "$d_1$". This LIOB is then followed by the creation of a cavitation bubble 14 (see FIG. 1) that will have a diameter "$d_2$". Inherently, it will happen that "$d_2$" is more than twice the size of "$d_1$" ($d_2 \geq 2d_1$). As noted above, during a procedure as envisioned by the present invention, the temporal influence of each cavitation bubble 14 will continue for a time period "$\tau$" that may be several microseconds in duration. During this time period "$\tau$", the bubble 14 will collapse to a substantially stationary diameter "$d_3$", with ($d_1 \leq d_3 \leq d_2$).

Figure 4:
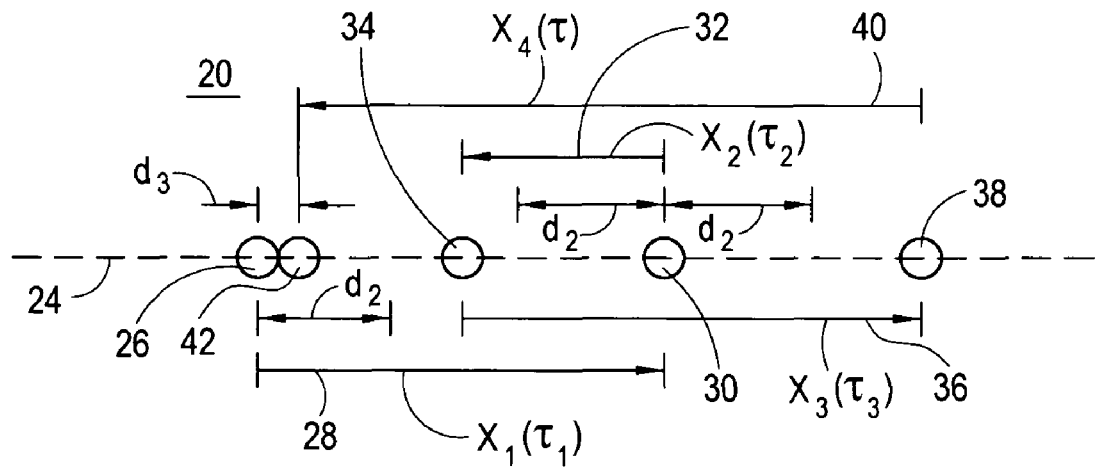
FIG. 4 is a pattern sequence for the spatial and temporal separation of laser beam focal spots in accordance with the present invention.

The operation of the present invention will, perhaps, be best appreciated with reference to FIG. 4. There it will be seen that a procedure in accordance with the present invention starts at time "$\tau_0$" (see FIG. 5) and at a predetermined location 26 in the material 20. Specifically, the procedure begins by focusing the laser beam 18 to induce LIOB with a focal spot 22 at the location 26. Then, during a time segment "$\Delta \tau$" ($\tau_0 + \Delta \tau = \tau_1$), the laser beam 18 is maneuvered on the move line 28 [$x_1(\tau_1)$], through a distance "$x_1$" to a location 30 in the material 20. The laser beam 18 is again focused to induce LIOB with another focal spot 22 at the location 30. This occurs at time "$\tau_1$" (see FIG. 5). It is an important aspect of the present invention that the distance "$x_1$" is greater than the diameter "$d_2$" of the cavitation bubble 14 that was created at location 26. Subsequently, during another time segment "$\Delta \tau$" ($\tau_0 + 2\Delta \tau = \tau_1 + \Delta \tau = \tau_2$), the laser beam 18 is maneuvered on the move line 32 [$x_2(\tau_2)$], through a distance "$x_2$" to a location 34 in the material 20. At time "$\tau_2$" the laser beam 18 is focused at the location 34 to induce LIOB with another focal spot 22. Similarly, the move line 36 [$x_3(\tau_3)$] in FIG. 4 indicates that the next LIOB occurs at a location 38 and, finally, the move line 40 [$x_4(\tau)$] shows that at the end of a time period "$\tau$", LIOB occurs at the location 42.

In the sequence of focal spots 22 just discussed, each of the distances "$x_1$", "$x_2$", "$x_3$", and "$x_4$", though not necessarily equal to each other, are each greater than the distance "$d_2$". Additionally, it is to be noted that the locations 30, 34, 38 and 42 are separated by more than the distance "$d_2$" from the locations of all of the earlier focal spots 22 that were created within the immediately preceding time period "$\tau$". Finally, it is also to be noted that LIOB at the location 42, at the time "$\tau$", is within a distance "$d_3$" from the location 26. As contemplated by the present invention, this juxtaposition of the locations 26 and 42 is possible because a time period "$\tau$" separates the inducement of LIOB at the respective locations 26 and 42. In this example, five different locations have been discussed. It is to be appreciated, however, the present invention envisions LIOB at many more, or fewer, such locations within a time period "$\tau$".

In overview, several important aspects of the present invention will be appreciated by reference to FIG. 4. First, each focal spot 22 is separated from every other focal spot 22 that is created within each time period "$\tau$", by a distance greater than "$d_2$". Once a first focal spot 22 is created, after the expiration of a time period "$\tau$", a second focal spot 22 may be located within a distance "$d_3$" from the first focal spot 22. Finally, a pattern 24 of focal spots 22 can be created using an "n" number of time periods "$\tau$".

Figure 5:
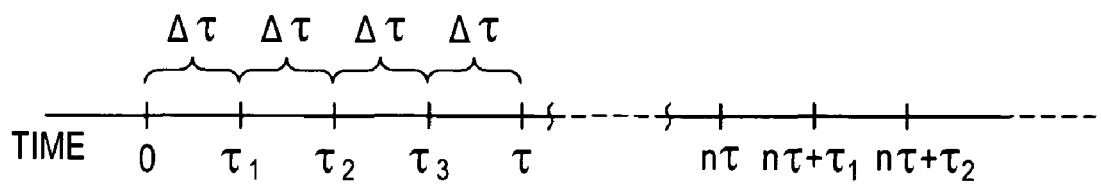
FIG. 5 is a time line for implementation of the sequence pattern shown in FIG. 4.
Figure 6:
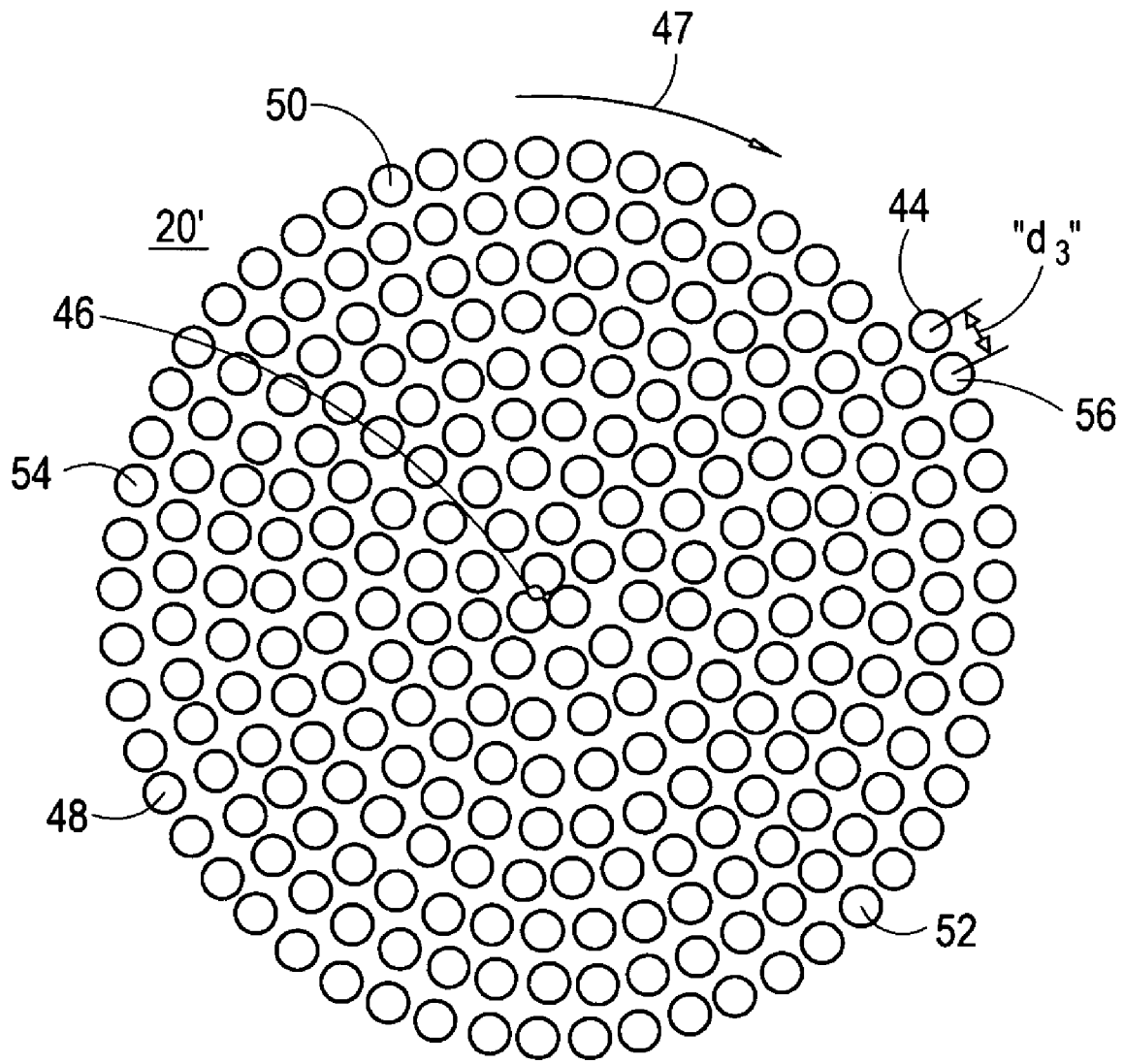
FIG. 6 is a schematic view of a spiral pattern of focal spots.

With cross-reference to FIGS. 5 and 6, the present methods are illustrated in an application in which a spiral pattern of LIOB focal spots is employed. Specifically, the procedure begins at time "$\tau_0$" (see FIG. 5) and at a predetermined location 44 in the material 20'. Specifically, the procedure begins by focusing the laser beam 18 (see FIG. 3) to induce LIOB with a focal spot 22 at the location 44. Then, during a time segment "$\Delta \tau$" ($\tau_0 + \Delta \tau = \tau_1$), the laser beam 18 is rotated about axis 46 and in the direction of arrow 47 to a location 48 in the material 20'. The laser beam 18 is again focused to induce LIOB with another focal spot 22 at the location 48. This occurs at time "$\tau_1$" (see FIG. 5). It is an important aspect of the present invention that the distance between location 44 and location 48 is greater than the diameter "$d_2$" of the cavitation bubble 14 that was created at location 44. Subsequently, during another time segment "$\Delta\tau$" ($\tau_0+2\Delta\tau=\tau_1+\Delta\tau=\tau_2$), the laser beam 18 is rotated to a location 50 in the material 20'. At time "$\tau_2$" the laser beam 18 is focused at the location 50 to induce LIOB with another focal spot 22. This process continues with successive LIOB inducements at location 52 and location 54. In this sequence of focal spots 22 the distances between locations 44, 48, 50, 52 and 54, though not necessarily equal to each other, are each greater than the distance "$d_2$". Additionally, it is to be noted that the locations 44, 48, 50, 52 and 54 are separated by more than the distance "$d_2$" from the locations of all of the earlier focal spots 22 that were created within the immediately preceding time period "$\tau$". At or after the time "$\tau$", LIOB can be induced at the location 56, which is within a distance "$d_3$" from the location 44, as shown. As contemplated by the present invention, this juxtaposition of the locations 44 and 56 is possible because a time period "$\tau$" separates the inducement of LIOB at the respective locations 44 and 56. This process can then be continued until LIOB is induced at each location in the spiral pattern.

While the particular Time-Resolved Scanning Patterns for Intrastromal Surgery as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for performing laser induced optical breakdown (LIOB) in a substantially transparent material which comprises the steps of:
    calculating a pattern for a succession of laser focal spots in the material, wherein LIOB occurs at each focal spot in a volume of material having a diameter "$d_1$", and the LIOB results in the generation of a cavitation bubble having a maximum diameter "$d_2$", where "$d_2$" is greater than "$d_1$", and a decay time "$\tau$" during which the cavitation bubble collapses to a substantially stationary diameter "$d_3$", with ($d_1 \leq d_3 \leq d_2$);
    inducing LIOB at a first focal spot in the pattern;
    inducing LIOB at an interim focal spot within the time period "$\tau$", wherein the center of the interim focal spot is at a distance greater than "$d_2$" from the center of the first focal spot and at a distance greater than "$d_2$" from the center of a second focal spot;
    waiting for a time period of "$\tau$"; and
    inducing LIOB at the second focal spot in the pattern after the time "$\tau$", wherein the second focal spot is substantially juxtaposed with the first focal spot at a distance less than "$d_2$" from the center of the first focal spot.

2. A method as recited in claim 1 further comprising the step of inducing LIOB at a plurality of interim focal spots within the time period "$\tau$", wherein each interim spot is at a distance greater than "$d_2$" from the center of every other interim focal spot.

3. A method as recited in claim 2 wherein the second focal spot becomes a first focal spot and each subsequent interim focal spot for LIOB is at a distance greater than "$d_2$" from all focal spots previously induced within a foregoing time period "$\tau$".

4. A method as recited in claim 1 wherein the distance "$d_1$" is in a range of 1 to 10 microns.

5. A method as recited in claim 4 wherein the distance "$d_2$" is approximately equal to $2d_1$ ($d_2 \cong 2d_1$).

6. A method as recited in claim 1 wherein the time period "$\tau$" is less than approximately two microseconds ($\tau \cong 2$ µs).

7. A method as recited in claim 1 wherein LIOB is induced by a laser pulse.

8. A method as recited in claim 7 wherein the laser pulse has a duration in a range of 1-1000 fs, an energy density in the range of 1-10 J/cm$^2$, and a focal spot diameter in the range of 1-10 microns.

9. A method for performing laser induced optical breakdown (LIOB) in a substantially transparent material which comprises the steps of:
    calculating a pattern for a succession of laser focal spots in the material, wherein LIOB occurs at each focal spot in a volume of material having a diameter "$d_1$", and the LIOB results in the generation of a cavitation bubble having a maximum diameter "$d_2$" and a decay time "$\tau$", where "$d_2$" is greater than "$d_1$";
    inducing LIOB at a first focal spot in the pattern;
    successively inducing LIOB at a plurality of interim focal spots in the pattern wherein the center of each interim spot is at a distance greater than "$d_2$" from the center of each interim focal spot previously induced within the time period "$\tau$"; and
    inducing LIOB at a second focal spot after time "$\tau$" and after LIOB at the first focal spot, wherein the second focal spot is juxtaposed with the first focal spot and the center of the second focal spot is at a distance "d" that is less than the distance "$d_2$" from the center of the first focal spot ($d < d_2$).

10. A method as recited in claim 9 wherein the second focal spot becomes a first focal spot.

11. A method as recited in claim 9 wherein the distance "$d_1$" is in a range of 1 to 10 microns, the distance "$d_2$" is approximately equal to $2d_1$ ($d_2 \cong 2d_1$), and the time period "$\tau$" is less than approximately two microseconds ($\tau \cong 2$ µs).

12. A method as recited in claim 9 wherein LIOB is induced by a laser pulse.

13. A method as recited in claim 12 wherein the laser pulse has a duration in a range of 1-1000 fs, an energy density in the range of 1-10 J/cm$^2$, and a focal spot diameter in the range of 1-10 microns.

14. A method as recited in claim 9 wherein the pattern is a spiral pattern.

15. A method as recited in claim 9 wherein LIOB at interim focal spots in the pattern is induced at a distance greater than $d_2$ from the center of each interim focal spot previously induced within the time period "$\tau$".

* * * * *

UNITED STATES PATENT AND TRADEMARK OFFICE
CERTIFICATE OF CORRECTION

PATENT NO. : 7,717,905 B2  Page 1 of 1
APPLICATION NO. : 10/978613
DATED : May 18, 2010
INVENTOR(S) : Frieder Loesel et al.

It is certified that error appears in the above-identified patent and that said Letters Patent is hereby corrected as shown below:

Column 6, Line 29
DELETE
"$"_1"$"
INSERT
--"$d_1$"--

Signed and Sealed this

Twenty-fourth Day of August, 2010

David J. Kappos
*Director of the United States Patent and Trademark Office*